(12) United States Patent
Willems

(10) Patent No.: US 11,460,389 B2
(45) Date of Patent: Oct. 4, 2022

(54) METHOD AND APPARATUS FOR TESTING RELATIVE HARDNESS OF HORIZONTALLY DISPLACED SURFACES

(71) Applicant: CTL Group, Skokie, IL (US)

(72) Inventor: Terry J. Willems, Kenosha, WI (US)

(73) Assignee: CONSTRUCTION TECHNOLOGY LABORATORIES, INC., Skokie, IL (US)

( * ) Notice: Subject to any disclaimer, the term of this patent is extended or adjusted under 35 U.S.C. 154(b) by 615 days.

(21) Appl. No.: 16/355,618

(22) Filed: Mar. 15, 2019

(65) Prior Publication Data

US 2019/0285526 A1 Sep. 19, 2019

Related U.S. Application Data

(60) Provisional application No. 62/761,324, filed on Mar. 16, 2018.

(51) Int. Cl.
*G01N 3/46* (2006.01)
*G01N 33/38* (2006.01)

(52) U.S. Cl.
CPC .......... *G01N 3/46* (2013.01); *G01N 33/383* (2013.01); *G01N 2203/0033* (2013.01)

(58) Field of Classification Search
CPC .................................. G01N 3/40; G01N 3/46
See application file for complete search history.

(56) References Cited

U.S. PATENT DOCUMENTS

| 2,279,264 | A | * | 4/1942 | Hoffman | G01N 3/46 73/78 |
| 2,801,540 | A | * | 8/1957 | Rondeau | G01N 3/46 73/150 R |
| 3,785,198 | A | * | 1/1974 | Heetman | G01N 3/46 73/78 |
| 3,937,069 | A | * | 2/1976 | Saunders | G01N 3/46 73/81 |
| 5,804,706 | A | * | 9/1998 | Williston | G01N 3/56 73/7 |
| 10,775,288 | B1 | * | 9/2020 | Bellemare | G01N 3/60 |
| 2004/0011119 | A1 | * | 1/2004 | Jardret | G01N 3/46 73/81 |
| 2010/0206041 | A1 | * | 8/2010 | Seok | G01N 3/46 73/7 |
| 2012/0103055 | A1 | * | 5/2012 | Ryan | G01N 3/46 73/7 |

(Continued)

FOREIGN PATENT DOCUMENTS

KR 20150074505 A * 7/2015

OTHER PUBLICATIONS

English Translation of KR-20150074505-A (Year: 2015).*

*Primary Examiner* — Alexander A Mercado
(74) *Attorney, Agent, or Firm* — Emerson, Thomson & Bennett, LLC; Roger D. Emerson

(57) ABSTRACT

An apparatus and method for testing relative hardness of horizontal concrete surfaces includes a weighted platform with scratching pins on a bottom surface of the platform. The pins are arranged in a trapezoidal arrangement. The apparatus is translated over the surface to determine if the surface has reached the desired level of hardness. If translation of the apparatus results in scratching of the surface, the desired level of hardness has not been reached.

9 Claims, 14 Drawing Sheets

(56) References Cited

U.S. PATENT DOCUMENTS

2014/0373608 A1* 12/2014 Bellemare ................ G01N 3/46
73/82
2016/0258852 A1* 9/2016 Bellemare ................ G01N 3/46

* cited by examiner

METHOD AND APPARATUS FOR TESTING RELATIVE HARDNESS OF HORIZONTALLY DISPLACED SURFACES

This application claims priority to U.S. Ser. No. 62/761,324 entitled "Device to Measure the Relative Hardness of Horizontal Concrete Surfaces", filed Mar. 16, 2018, which is incorporated herein by reference.

I. BACKGROUND OF THE INVENTION

A. Field of Invention

This invention pertains to the art of methods and apparatuses for testing, and specifically a method and apparatus for testing the relative hardness of planar surfaces, and most specifically, horizontal concrete surfaces.

B. Description of the Related Art

It is known in the art to test concrete surfaces by scratching them with a manually-held and manually-operated screwdriver.

The present invention provides methods and apparatuses for repeatable measurement of the desired surface, specifically, horizontally-oriented concrete surfaces.

II. SUMMARY OF THE INVENTION

According to one aspect of the present invention, a new and improved apparatus and method of using same is provided which provides for more repeatable testing data.

One advantage of this invention is the repeatability of the data.

Another advantage of the invention is improved safety, as a workman wielding a screwdriver or other sharp implement to gauge surface conditions is likely more dangerous than operating the invention disclosed in this document.

Still other benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, embodiment of which will be described in detail in this specification and illustrated in the accompanying drawings which form a part hereof and wherein.

IV. DETAILED DESCRIPTION OF THE INVENTION

Figure 3:
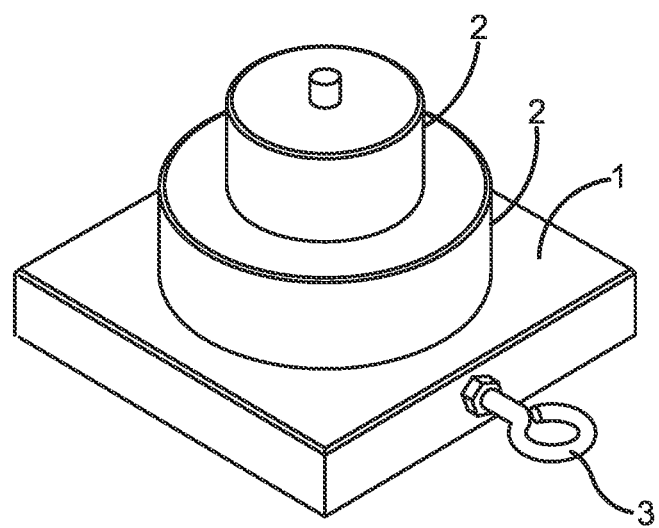
FIG. 3 is a schematic, perspective view of the invention, showing an embodiment of the device where the platform is further weighted by a first and second weighting disk.

Referring now to the drawings wherein the showings are for purposes of illustrating embodiments of the invention only and not for purposes of limiting the same, the inventive apparatus 10 comprises a platform 12. The platform is preferably generally rectangular in shape and has an upper surface 14, a lower surface 16, first, second, third, and fourth side surfaces respectively 18, 20, 22, and 24. The first side surface 18 is adapted to receive and mount an attachment device 30. With reference to FIG. 3, one preferred attachment device is shown, which is a hook-up device 31 having an eyelet 32 at a first end 36 and having a threaded connection 38 at a second end 34.

Figure 4:
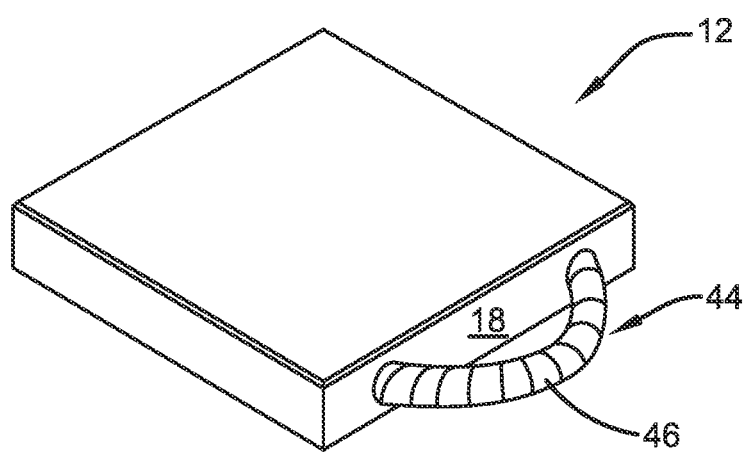
FIG. 4 is a schematic view of another embodiment of the invention showing a platform and a hookup comprising a rope or cable pull.
Figure 5:
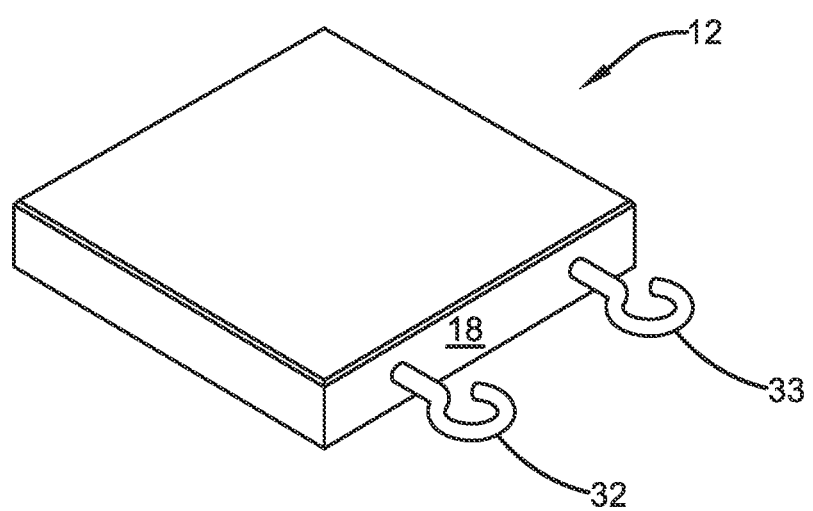
FIG. 5 is an alternate embodiment of the platform showing two hookups.
Figure 6:
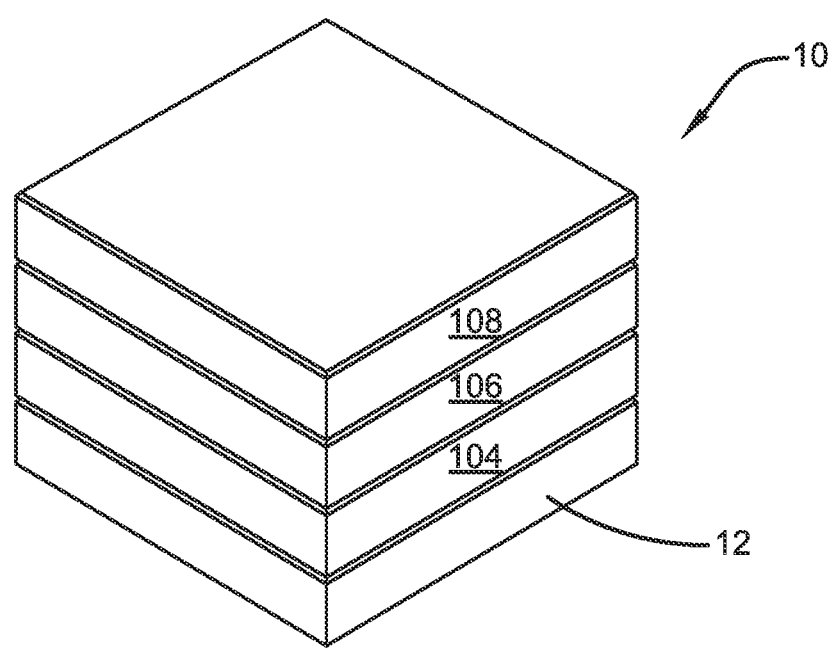
FIG. 6 is an alternate embodiment of the invention showing stackable weights 104, 106, and 108 of a rectangular orientation.

With reference to FIGS. 4 and 5, alternate attachment devices are shown. For example, with reference to FIG. 5, one attachment device features two hook-ups 32, 33 disposed across the first surface 18. With reference to FIG. 4, another attachment device 44 comprises a cable 46 attached via two threaded attachments to the first side surface 18. Other attachment means are within the skill of an ordinary engineer. The attachment devices allow the apparatus 10 to be translated horizontally across a generally flat surface by pulling the apparatus across the associated surface 50.

With continued reference to FIGS. 1-13, the platform 12 is preferably made of a relatively durable, hard, and heavy material. In one embodiment, the platform is made of 1018CF and preferably coated with hard chrome. The preferred dimensions are 1.09 inches in height, four inches square, and a center hole of 0.5 inches in diameter. One embodiment of the platform weighs 20 lbs. In some situations, and in some applications, additional weight might be desired. In such case, a pin 54 can be affixed to the upper surface 14 of the platform 12 to facilitate selectively receiving additional weights.

Figure 1:
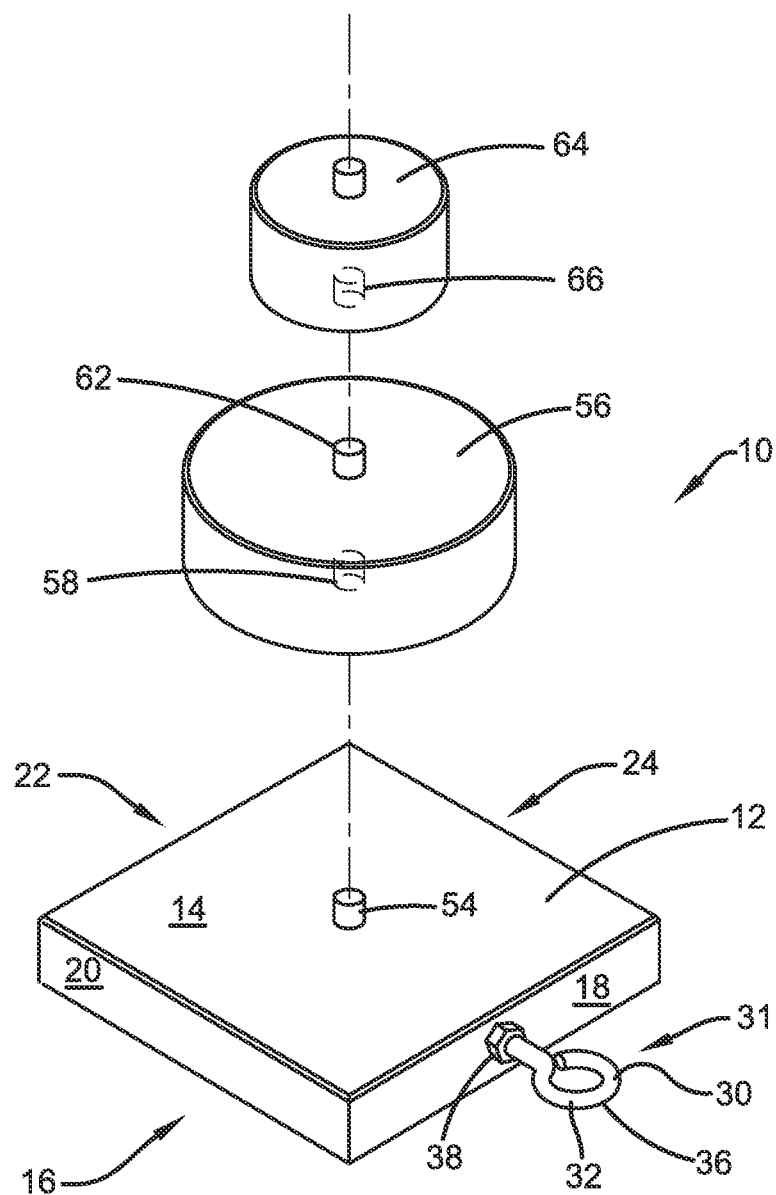
FIG. 1 is an exploded schematic view of one embodiment of the apparatus which shows a platform as well as two additional disks.
Figure 2:
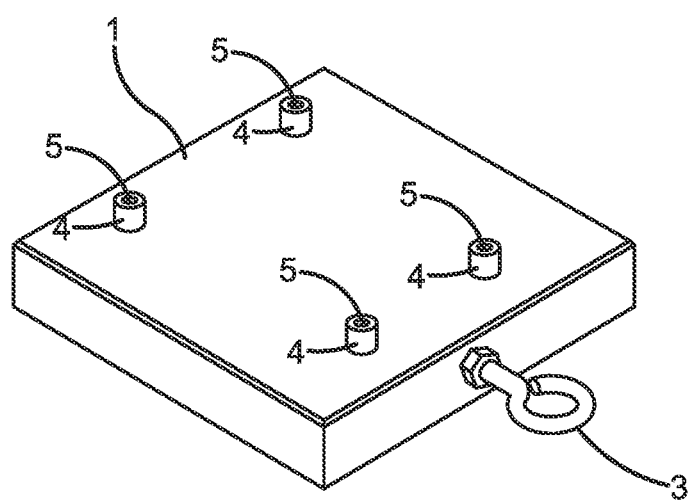
FIG. 2 is a schematic view of the underside of the platform, showing the trapezoidal configuration of the scratching pins.

In an embodiment shown in FIG. 1, the additional weight is in the form of a first weighting disk 56 which has a hole 58 which receives pin 54. In one embodiment, the disk 52 also has a pin 62 able to receive and operatively engage a second weighting disk 64 through a hole 66. In such way, weights can be added or removed depending on the application. In the embodiment shown in FIG. 1, the additional weight is shown in the form of the first weighting disk and the second weighting disk 64. Note that the diameter of the first weighting disk 56 is less than the width of the platform 10 and the diameter of the second weighting disk 64 is less than that of the first weighting disk 56. This "pyramid" configuration may help the stability of the platform 12, as the apparatus 10 is pulled across the associated surface 50.

Figure 8:
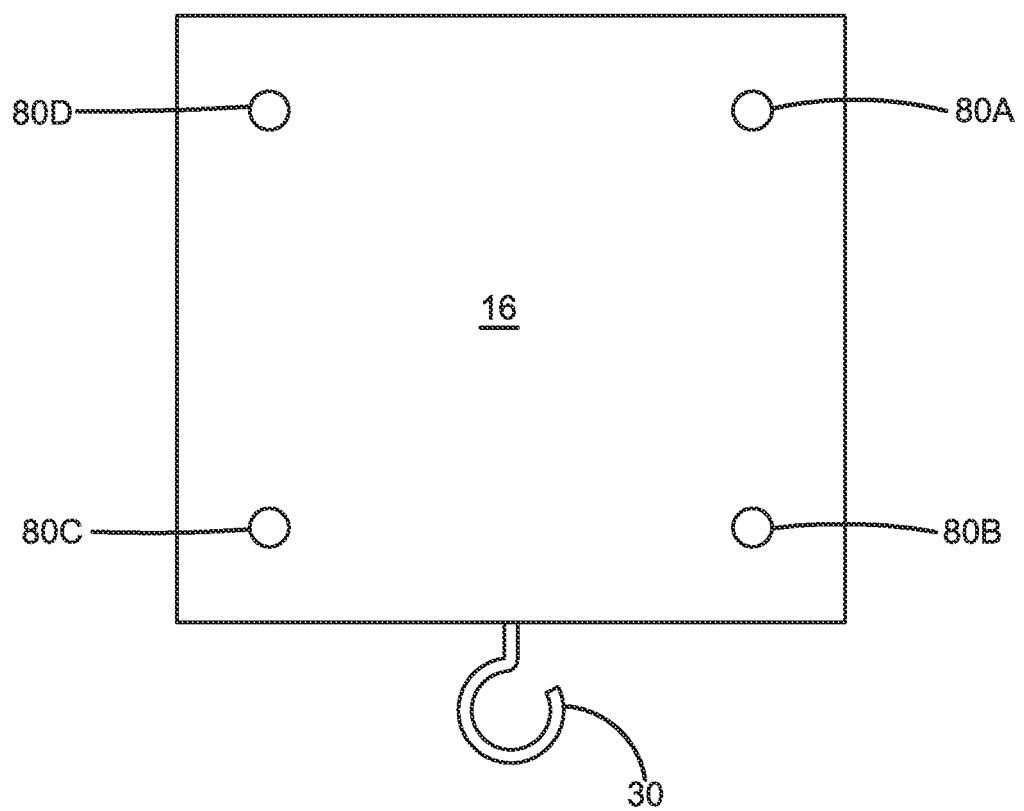
FIG. 8 is a schematic representation of the underside of the platform showing a preferred location of scratching pins, and the preferred trapezoidal configuration.
Figure 9D:
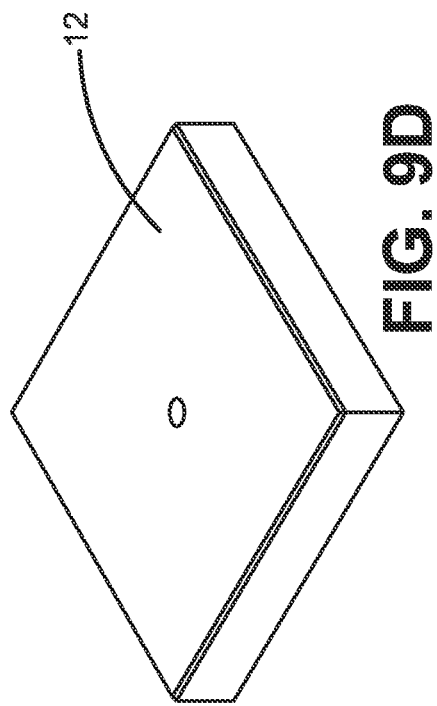
FIG. 9 is a drawing of the platform, with FIG. 9A being a top view, FIG. 9B being a side view, FIG. 9C being a bottom view and FIG. 9D being a perspective view of the platform.
Figure 9A:
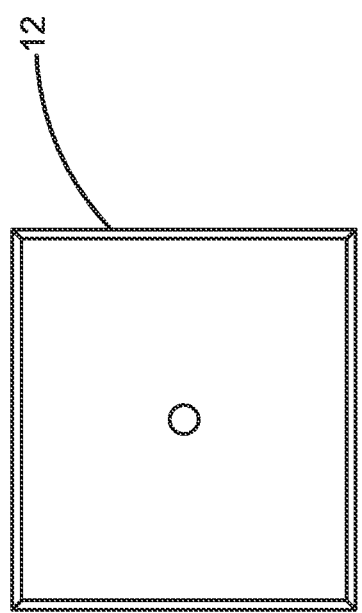
Figure 9B:
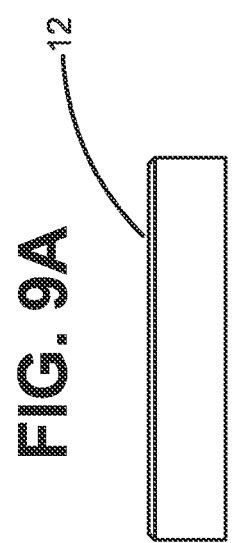
Figure 9C:
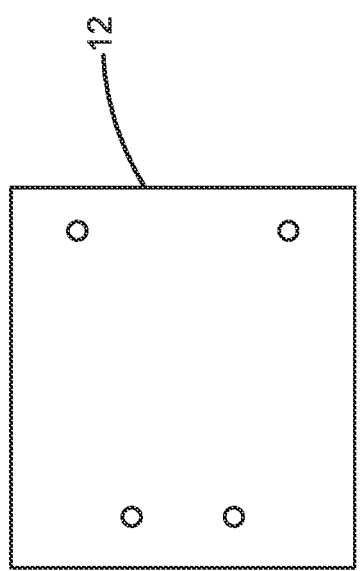
Figure 10D:
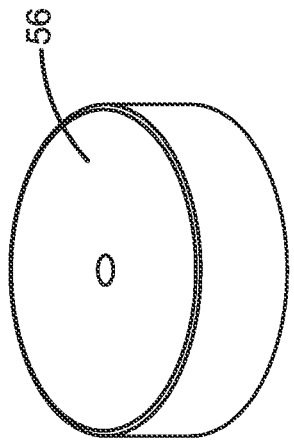
FIG. 10 is a drawing of a first weighting disk, with FIG. 10A being a top view, FIG. 10B being a side view, FIG. 10C being a bottom view and FIG. 10D being a perspective view of the weighting disk.
Figure 10A:
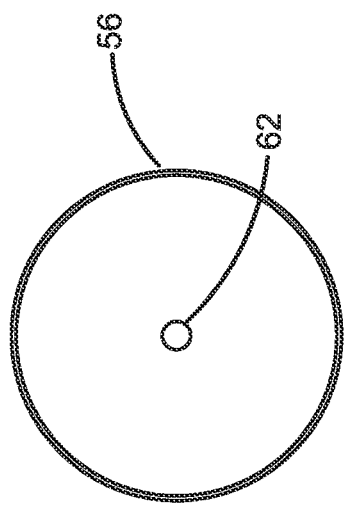
Figure 10B:
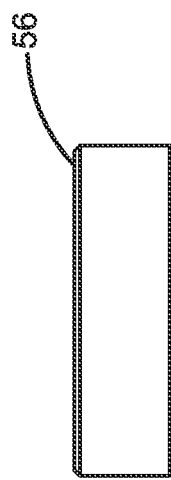
Figure 10C:
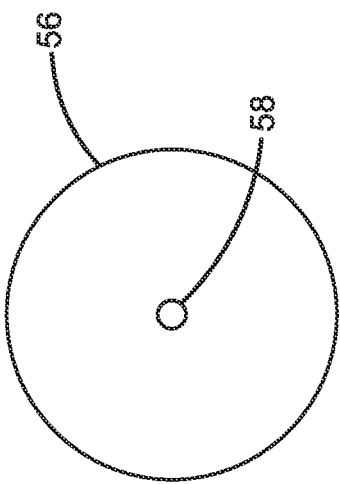

The number of scratching pins 80 is preferably at least three, so as to define a plane and enable the platform 12 to sit in a stable orientation on the associated surface 50. The preferred material for the scratching pins is O1 tool steel which has been heat-treated to Rc 54-56. However, the currently preferred embodiment features four scratching pins arranged near the corners of the platform 10 as shown in FIG. 8. Moving the pins closer to the center of the platform tends to make the platform less stable and so a preferred arrangement is as shown. The preferred orientation is four pins 80A, 80B, 80C and 80D in a trapezoidal configuration, as shown in FIG. 8. The benefit of this orientation is to decrease the likelihood of a scratch from one pin, e.g., 80A, being coincident with the scratch of another pin, e.g., 80B.

Figure 7C:
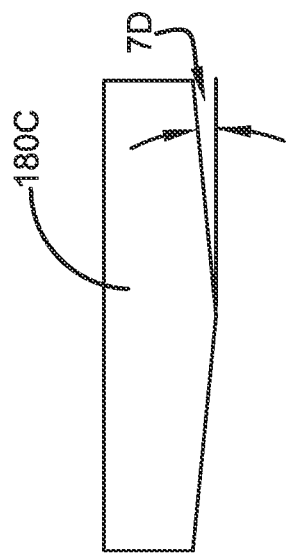
FIG. 7 is a schematic side view representation of different embodiments of scratching pins, showing a first variety, second and a third embodiments.
Figure 7B:
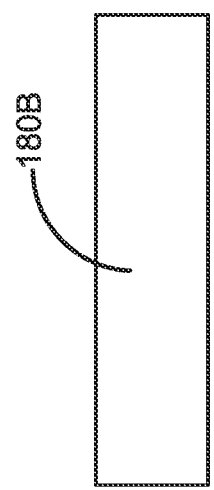
Figure 7A:
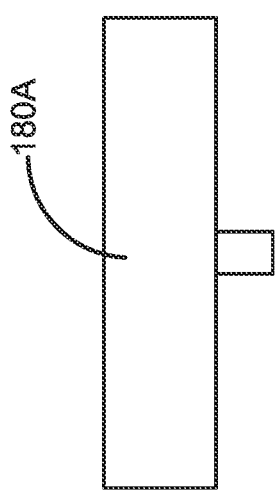

With reference to FIG. 7, various configurations of scratching pins 180a, 180b, and 180c are contemplated and shown.

With reference to FIGS. 9-12, the dimensions and orientation of the major components are shown.

With reference to FIG. 9, in the preferred embodiment, the dimensions for platform 12 are 1.09 inches in height, four inches square, and a center hole of 0.5 inches in diameter.

With reference to FIG. 10, in the preferred embodiment, the first weighting disk 56 has a diameter of six inches and a thickness of 1.25 inches. The center hole 58 has a diameter of 0.625 inches and the top pin 56 has a diameter of 0.5 inches. The first weighting disk weighs 10 lbs.

Figure 11C:
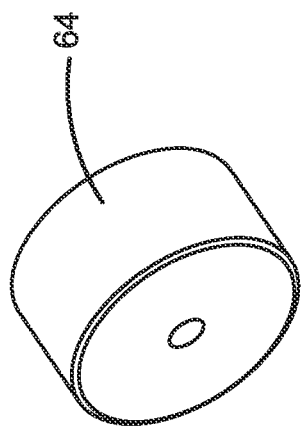
FIG. 11 is a drawing of a second weighting disk, with FIG. 11A being a top view, FIG. 11B being a side view, and FIG. 11C being a perspective view of the weighting disk.
Figure 11A:
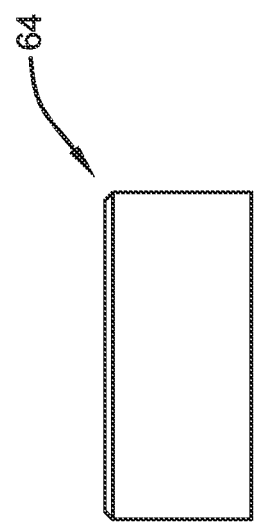
Figure 11B:
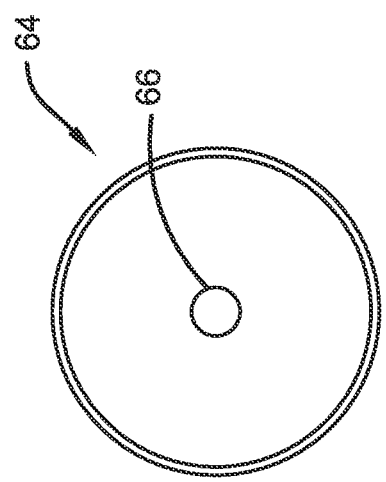
Figure 12A:
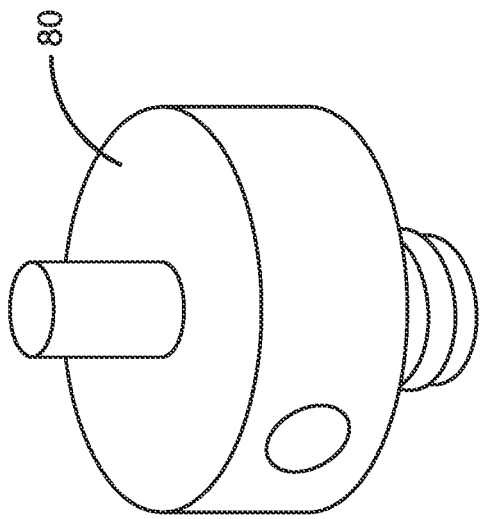
FIG. 12 is a drawing of a scratching pin, with FIG. 12A being a top view, FIG. 12B being a side view, FIG. 12C being another side view 90 degrees from FIG. 12B, and FIG. 12D being a perspective view of the scratching pin.
Figure 12D:
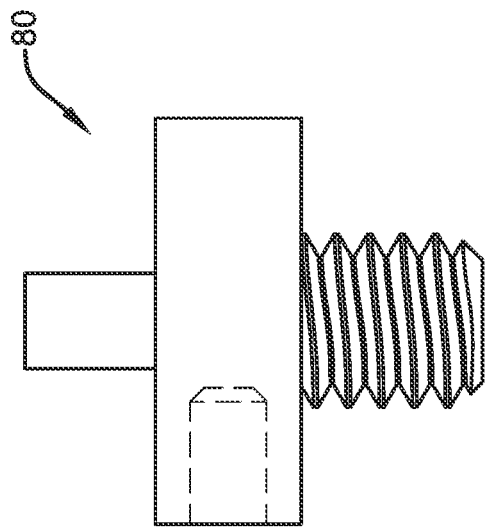
Figure 12B:
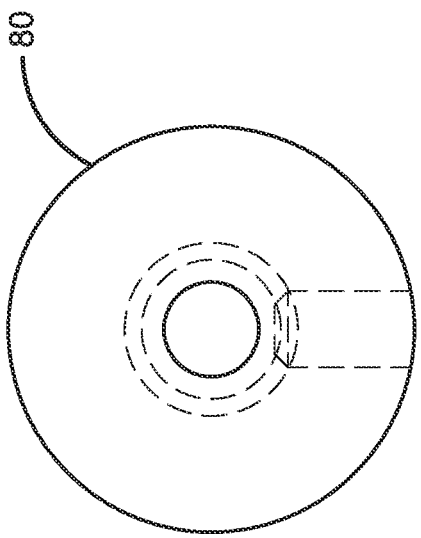
Figure 12C:
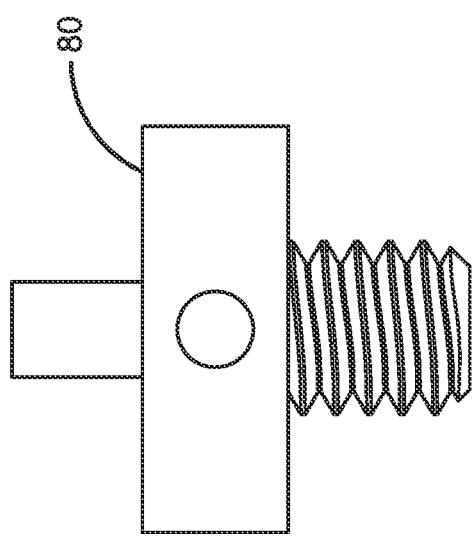
Figure 13D:
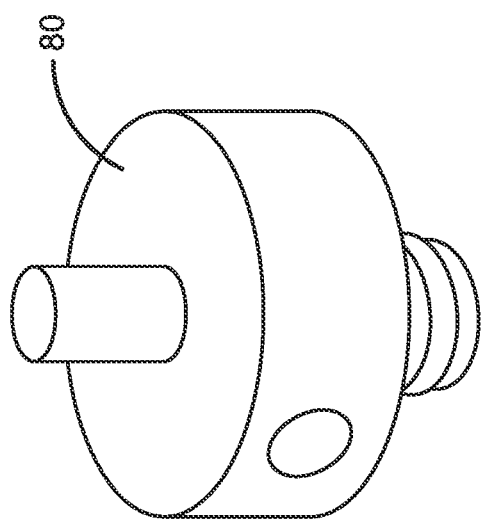
FIG. 13 is a shop drawing of a scratching pin, showing the relevant dimensions.
Figure 13C:
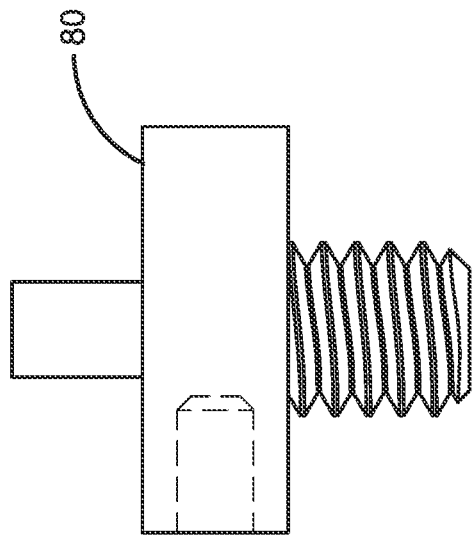
Figure 13A:
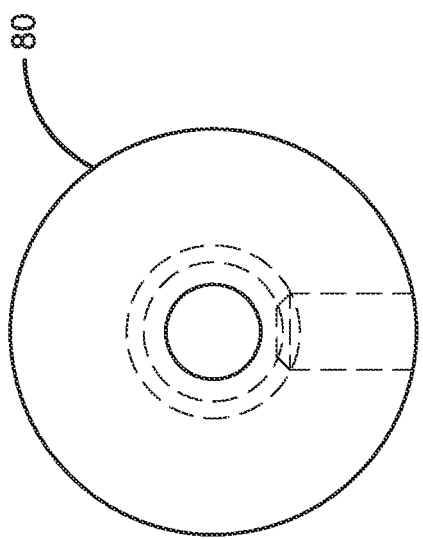
Figure 13B:
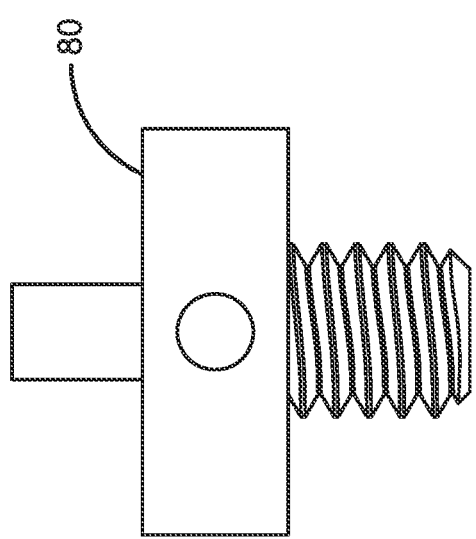

With reference to FIG. 11, in the preferred embodiment, the second weighting disk 64 has a diameter of 3.5 inches and a thickness of 1.83 inches. The center hole 66 has a diameter of 0.625 inches. The second weighting disk weighs 5 lbs.

With reference to FIG. 12, in the preferred embodiment, the scratching pin 80 has dimensions as shown in the FIG. 13.

The preferred method of operating the apparatus 10 will now be discussed. When the relative hardness generally planar surface is to be evaluated, an appropriate design of scratching pin is selected and screwed into the lower surface 16 of the platform 12. Next, an appropriate amount of weight is determined, and if additional weights are needed, they are added. Next, the platform is pulled across the surface. One easy way to do this is for a rope, strap, or cable to be attached to one of the attachment devices shown herein. A human, using manually operated forces, can pull the attachment means across a surface, such as concrete. Other applications have a robot or a machine pulling the apparatus across the desired surface. For example, a lapse setting, the apparatus could be pulled across a planar substrate of plastic or metal. However, the primary application for this device is industrial concrete floor slabs, using manually generated forces, to pull the apparatus across concrete.

The benefit of such an analysis is to determine whether if the floor slab has been finished to the desired hardness to resist abrasion and perform as intended.

Figure 14B:
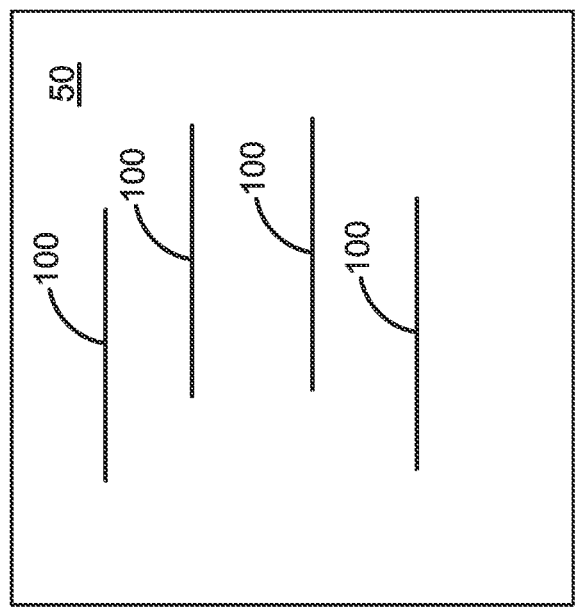
FIG. 14 is a schematic drawing of exemplary scratches, with FIG. 14A showing deeper scratches and FIG. 14B showing less deep scratches.
Figure 14A:
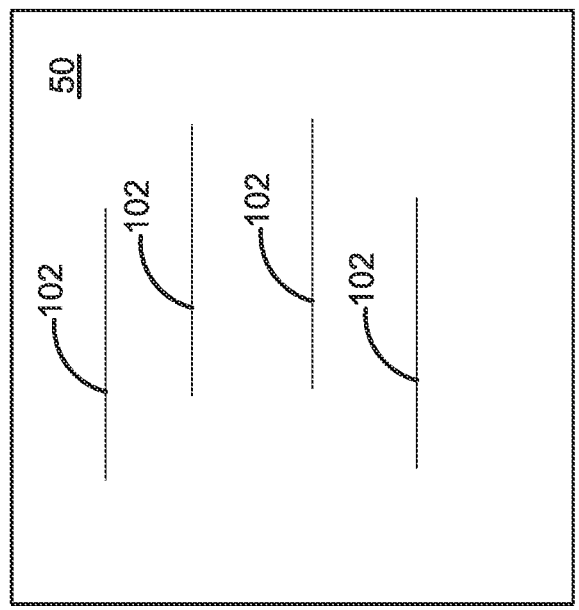

With reference to FIG. 14A, the apparatus and scratching pins are schematically shown scoring or scratching the associated surface 50 of the concrete and the result of the scratches 100 communicate to the contractor that the relative hardness of the concrete has not been obtained as designed. A concrete surface that exhibits the proper hardness will not be scratched by the device with all the weights installed (i.e, when the device has a weight of 35 lbs).

The embodiments have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

Having thus described the invention, it is now claimed:

1. An apparatus for determining the relative hardness of a horizontal concrete surface, the apparatus comprising:
   a. a platform, said platform being square and having a height between 0.25 inches and 6 inches, a width between 2.00 inches and 14.00 inches, and a depth between 2.00 inches and 14.00 inches; said platform being made of steel and having a weight between 2 pounds and 100 pounds; said platform having an upper surface, a lower surface, and first, second, third and fourth side surfaces; said lower surface having four receptacles for selectively receiving a first end of scratching pins, said receptacles being in a trapezoidal pattern located between 0.5 inches and 6 inches from one said of side surfaces; said receptacles having an interior bore; said upper surface having a first receptacle located in the center of the upper surface of the platform, said first receptacle in said upper surface having an interior bore and therein selectively receiving a first attachment pin, said first attachment pin being cylindrical and having a diameter;
   b. a first weighting disk, said first weighting disk having an upper surface, a lower surface, and side surface; said lower surface having a threaded receptacle for selectively receiving a second end of said first attachment pin in said platform, said threaded receptacle in said first weighting disk being located at the center of the lower surface of the first weighting disk; said threaded receptacle in said lower surface of said first weighting disk having an interior bore; said upper surface of said first weighting disk having a first receptacle located in the center of said upper surface of said first weighting disk, said first receptacle in said upper surface being threaded and having an interior bore and therein selectively receiving a second attachment pin, said second attachment pin in said first weighting disk being cylindrical, said first weighting disk having a diameter between 2 inches and 12 inches and a thickness between 0.25 inches and 4 inches, and having a center hole having a diameter of between 0.25 inches and 1.25 inches;
   c. a second weighting disk, said second weighting disk having an upper surface, a lower surface, and side surface; said lower surface having a threaded receptacle for selectively receiving a second end of said second attachment pin in said first weighting disk, said threaded receptacle in said second weighting disk being located at the center of the lower surface of said second weighting disk; said threaded receptacle in said lower surface of said second weighting disk having an interior bore; said upper surface of said second weighting disk having a first receptacle located in the center of said upper surface of said second weighting disk, said first receptacle in said upper surface being threaded and having an interior bore and therein selectively receiving a first end of a lifting device;

d. said scratching pins extending outwardly and downwardly from said lower surface of said platform; and, e. an attachment device, having first and second ends; said attachment device being selectively attached to said first side surface of said platform; said first side surface having a threaded receptacle for selectively receiving said second end of said attachment device, said threaded receptacle in said first side surface of said platform being located at the center of said first side surface of said platform.

2. An apparatus for determining a condition of a surface, the apparatus comprising:

a. a platform, said platform having an upper surface, a lower surface, and first, second, third and fourth side surfaces; said lower surface having a plurality of receptacles for selectively receiving a first end of a respective plurality of scratching pins arranged in a predetermined orientation on the lower surface of the platform;

b. a first weighting member, said first weighting member having an upper surface, and a lower surface; said lower surface being configured to be selectively attached to said platform;

c. a second weighting member, said second weighting member having an upper surface, and a lower surface; said lower surface being configured to be selectively attached to said first weighting member;

d. said scratching pins extending outwardly and downwardly from said lower surface of said platform and arranged sufficiently near corners of the platform to enable the platform to sit in a stable orientation on the associated concrete surface; and, e. an attachment device selectively attached to said first side surface of said platform, so that said platform is translated across the associated surface.

3. The apparatus of claim 2, wherein the plurality of receptacles and the respective plurality of scratching pins is four.

4. The apparatus of claim 3, wherein the predetermined orientation of the four scratching pins is in a trapezoidal configuration to decrease likelihood of a scratch from one pin being coincident with a scratch of another pin.

5. The apparatus of claim 2, wherein at least one of the scratching pins is selected from a plurality of scratching pin configurations.

6. The apparatus of claim 2, wherein at least one of the scratching pins is made of O1 tool steel which has been heat-treated to Rc 54-56.

7. A method of determining whether concrete has achieved a desired level of hardness, said method comprising the steps of:

a. selecting at least one desired scratching pin from a plurality of scratching pins and affixing said pin to a platform;

b. selecting a desired weight and affixing said weight to said platform;

c. placing said platform on an associated concrete surface;

d. translating said platform across the associated concrete surface;

e. evaluating the associated concrete surface to determine if any scratches have been achieved; and, f. determining whether the associated concrete surface has been finished to the desired hardness to resist abrasion and perform as intended based on whether any scratches have been achieved.

8. The method of claim 7 wherein said translating is by placing a tensile force on said platform by pulling said platform.

9. The method of claim 7, wherein the step of determining comprises determining that the associated concrete surface exhibits proper hardness if it will not be scratched by the desired scratching pin with the desired weight.

* * * * *